United States Patent [19]

Duck et al.

[11] Patent Number: 5,011,769
[45] Date of Patent: * Apr. 30, 1991

[54] METHODS FOR DETECTING NUCLEIC ACID SEQUENCES

[75] Inventors: Peter Duck; Robert Bender, both of Ottawa, Canada

[73] Assignee: Meiogenics U.S. Limited Partnership, Columbia, Md.

[*] Notice: The portion of the term of this patent subsequent to Oct. 24, 2006 has been disclaimed.

[21] Appl. No.: 187,814

[22] Filed: Apr. 29, 1988

Related U.S. Application Data

[63] Continuation-in-part of Ser. No. 805,279, Dec. 5, 1985, Pat. No. 4,876,187.

[51] Int. Cl.$^5$ .................... C12Q 1/68; C12Q 1/42; G01N 33/566; C07H 15/12
[52] U.S. Cl. .................................... 435/6; 435/19; 435/21; 436/501; 536/26; 536/27; 536/28; 935/77; 935/78
[58] Field of Search ............... 435/6, 19, 21; 436/501; 536/26, 27, 28; 935/77, 78

[56] References Cited

U.S. PATENT DOCUMENTS 4,795,701 1/1989 Vary .................................. 935/78 X
4,820,630 4/1989 Taub ................................. 935/78 X

FOREIGN PATENT DOCUMENTS 0227976 8/1987 European Pat. Off. .

Primary Examiner—Jack Spiegel

[57] ABSTRACT

This invention provides a method for detecting a target nucleic acid which comprises forming a reaction mixture which includes the target nucleic acid and an amount of a complementary single-stranded nucleic acid probe which is greater than the target molecule, under conditions which allow the probe and the target nucleic acid to hybridize to each other and form a double stranded target-probe complex, nicking the hybridized probe at least once within a predetermined sequence so as to form at least two probe fragments hybridized to the target nucleic acid, resulting in the probe fragments to become single-stranded and allowing the target nucleic acid to become hybridized to another probe; and identifying probe fragments, thereby detecting the target nucleic acid. This invention also provides a method for detecting a target nucleic acid.

12 Claims, 1 Drawing Sheet

METHODS FOR DETECTING NUCLEIC ACID SEQUENCES

This application is a continuation-in-part of U.S. Application Ser. No. 805,279, filed Dec. 5, 1985, U.S. Pat. No. 4,876,187, the contents of which are hereby incorporated by reference.

BACKGROUND OF THE INVENTION

Throughout this application, various patents and publications are references and citations provided for them. The disclosure of these patents and publications in their entireties are hereby incorporated by reference into this application to more fully describe the state of the art to which this invention pertains.

Much of the disclosure of U.S. Application Ser. No. 805,279 has also been published. See, e.g., European Patent Application No. 86116906.8, published Aug. 7, 1987.

Current DNA probe methodology basically involves attaching target DNA to a nitrocellulose filter by bringing it into contact with the filter directly or via the Southern transfer technique from an agarose gel. The DNA is then denatured and the filters baked to ensure firm attachment. Generally, the preparation of the DNA and the running of the gels is a time consuming, costly process requiring a reasonably high technical skill level.

The next step is to prepare the probe DNA. Probe DNA is prepared by labelling radioactively specific DNA by nick translation, polynucleotide kinase, or some other polymerase type copy reaction using nucleotides labelled with $^{32}P$. Once prepared, the probe DNA is permitted to hybridize with the bound target DNA. Hybridization is allowed to proceed at a suitable temperature, typically for several hours. The DNA probe will associate to form hybrid duplexes with any of the bound target DNA that has complementary base sequences. Extraneous material, including unbound probe DNA, is then washed away from the filter and the filter is then exposed to film sensitive to the radioactive label.

European Patent Application Publication No. 0 067 597, (Bender et al.) published Dec. 22, 1982 discloses oligonucleotides and a process for their preparation which comprises incorporating ribonucleotide units at specific locations in deoxyribonucleotide chains to provide predetermined cleavage sites which allow ease of chain cleavage. Although the products from their process are said to be useful for separating mixtures of nucleotide and polynucleotide products, Bender et al. do not teach a method for detecting target nucleic acid molecules based upon the amplification of probe fragments.

International Patent Application No. WO 84/03520 (Malcom et al.), published Sept. 13, 1984 discloses a method of detecting nucleic acid sequences which utilizes tandem hybridization of a nucleic acid probe and an enzyme containing marker. The method involves contacting the probe with a sample containing a complementary target sequence under hybridizing conditions. Before or after hybridization with the target sequence, the probe is attached by hybridization to an enzyme labelled marker polynucleotide which has a sequence complementary to a sequence on the probe.

U.S. Pat. No. 4,358,535 (Falkow et al.) discloses radioactively labeled nucleotide probes which are complementary to a target nucleic acid sequence of interest and a method of using these probes to detect the presence of a pathogen from which the target nucleic acid sequence is derived. The method comprises first fixing the target nucleic acid sequence to an inert support before hybridization with the probe. Next, the fixed nucleic acid is contacted with the radioactively labeled probe under hybridizing conditions, with hybridization taking place on the solid support. Then, the presence of the target nucleic acid sequence is determined by detecting the presence of any label on the inert support. A disadvantage of such a system is that the probe itself cannot be immobilized. If the probe of Falkow et al. is immobilized, rather than the target nucleic acid sequence, then the label molecules of the immobilized probe will be bound to the solid support regardless of whether the probe has hybridized with a target nucleic acid sequence. The result would not permit the detection of the presence of target nucleic acid.

European Patent Application Publication No. 0 117 440 discloses non-radioactive chemically labeled polynucleotide probes and methods of using the probes. The methods disclosed are similar to the method of Falkow et al. in that the target nucleic acid sequence is fixed to a solid support before hybridization.

Recently, other detection systems have been developed, such as fluorescent tags or color change enzyme systems. However, such systems have had significant problems with sensitivity and background levels (noise).

U.S. Pat. No. 4,362,867 (Paddock) discloses a hybrid nucleic acid construction which comprises two complementary deoxynucleotide sequences which are hybridized to form a double-stranded helical structure. Situated between and covalently bonded to the two deoxynucleotides is a ribonucleotide sequence. The construction forms a single unit, in which none of the nucleotide sequences repeat themselves.

U.S. Pat. No. 4,683,195 (Mullis, et al.) discloses a process for amplifying and detecting target nucleic acid sequences comprising treating separate complementary strands of the nucleic acid with a molar excess of two olignucleotide primers. By extending the primers to form complementary primer extension products which act as templates for synthesizing the desired nucleic acid sequence, the sequence so amplified is detected. A disadvantage of this process is the requirement of thermal cycling and the lack of constant temperature conditions.

In U.S. pat. No. 4,683,194 (Saiki et al.), a method is disclosed for detectiong the presence or absence of a specific site in a nucleic acid sequence using an oligonucleotide probe that is complementary to one strand of the nucleic acid sequence spanning the restriction site. Saiki et al. teach that their nucleic acid, i.e., oligonucleotide, probe, may be used as is or the sequence it contains can be amplified to increase sensitivity using the process disclosed in U.S. Pat. No. 4,683,202. Such an amplifying process suffers from the disadvantages inherent in U.S. Pat. No. 4,683,195, discussed above.

SUMMARY OF THE INVENTION

The present invention provides a method for detecting a target nucleic acid molecule which comprises: (a) forming a reaction mixture which includes the target nucleic acid molecule and an amount of a complementary single-stranded nucleic acid probe which is greater than the target molecule, under conditions which allow the probe and the target nucleic acid molecule to hybridize to each other and form a double-stranded target-probe complex; (b) nicking the hybridized probe at least once within a predetermined sequence so as to form at least two probe fragments hybridized to the target nucleic acid molecule, resulting in the probe fragments to become single-stranded and allowing the target nucleic acid molecule to become hybridized to another probe; and (c) identifying probe fragments, thereby detecting the target nucleic acid molecule The present invention also provides a method for detecting a target deoxyribonucleic acid molecule which comprises: (a) forming a reaction mixture which includes the target deoxyribonucleic acid molecule and a single-stranded nucleic acid probe having a ribonucleotide sequence complementary to the target deoxyribonucleic acid molecule which may be covalently bound at one or both of its termini to one or more deoxyribonucleotides which may or may not be complementary to the target deoxyribonucleic acid molecule under conditions which allow the probe and the target deoxyribonucleic acid molecule to hybridize to each other and form a double-stranded target-probe complex; (b) nicking the hybridized probe at least once within a predetermined sequence so as to form at least two probe fragments hybridized to the target deoxyribonucleic acid molecule, resulting in the probe fragments to become single-stranded and allowing the target nucleic acid molecule to become hybridized to another probe; and (c) identifying probe fragments, thereby detecting the target deoxyribonucleic acid molecule.

Figure 1:
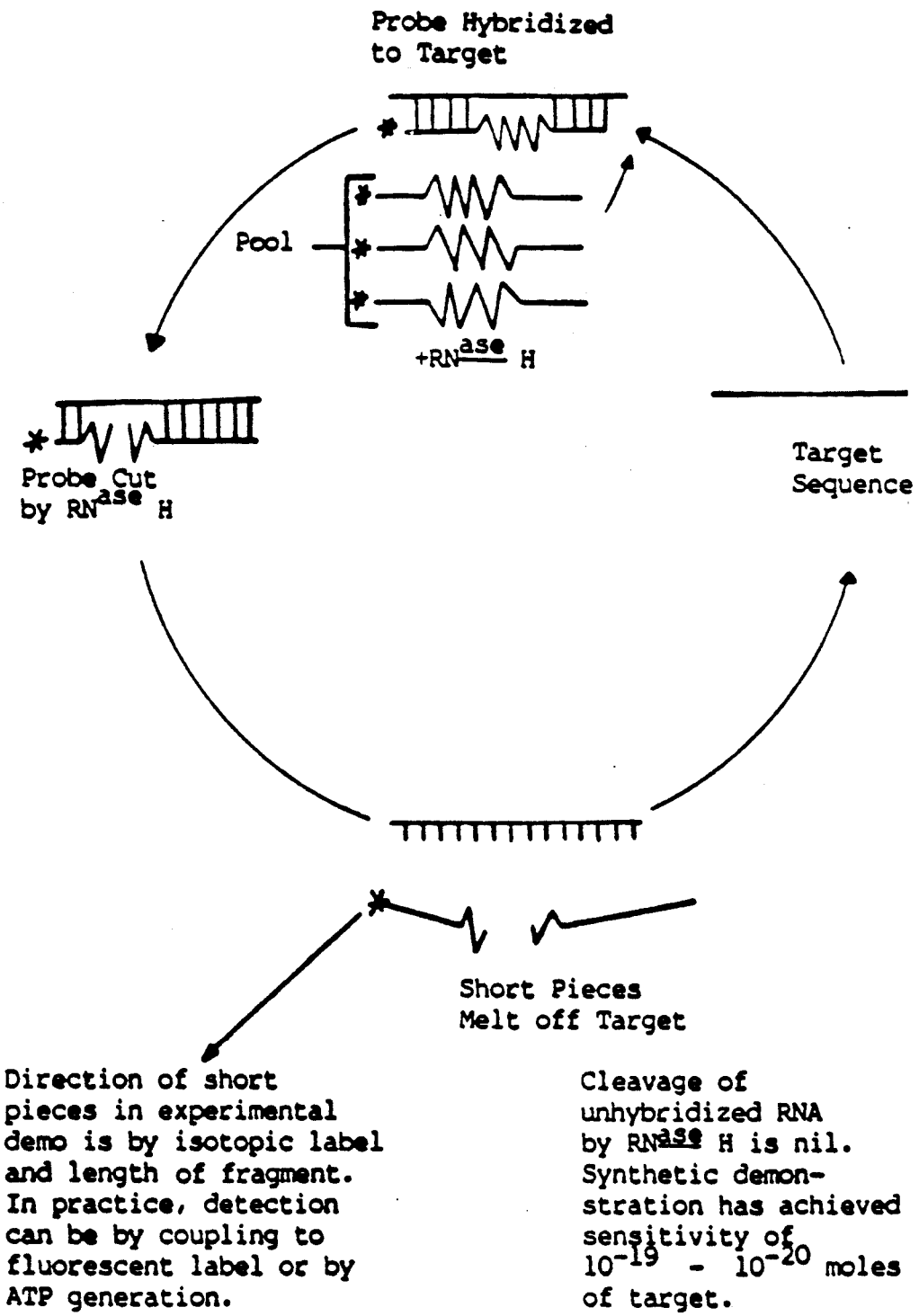
FIG. 1 depicts the use of a nucleic acid probe as a self-amplifing and cycling construction in the method of the present invention for detecting target nucleic acid molecules.

A pool of nucleic acid probes and a ribonuclease, e.g., RNase H, are reacted with a sample which contains a target nucleic acid molecule. The single-stranded nucleic acid probe is complementary to and in an amount greater than the target nucleic acid molecule. Double-stranded target-probe complexes are formed as the result of hybridization. RNase H nicks or excises out RNA sequences in hybridized double-stranded RNA-DNA.

As a consequence of such nicking, the remaining DNA probe fragments are "melted" off, i.e., become unhybridized, from the target molecule. The resulting single-stranded probe fragments are detectable by isotopic labelling or by the length of the probe fragment, i.e., by direct measurement. In practice, the probe fragments can be detected by coupling to fluorescent labels which have been initially placed on the nucleic acid probes or by ATP generation using single phosphorylated nucleotides, e.g., adenosine monophosphate, which have been formed. Additional probe molecules may react with the now free target molecules to complete the cycling sequence. RNase H does not nick or cleave unhybridized RNA. By using such a system of cycling, sensitivity of from about $10^{-19}$ to about $10^{-20}$ moles of target can be attained.

DETAILED DESCRIPTION OF THE INVENTION

The present invention provides a method for detecting a target nucleic acid molecule which comprises: (a) forming a reaction mixture which includes the target nucleic acid molecule and an amount of a complementary single-stranded nucleic acid probe which is greater than the target molecule, under conditions which allow the probe and the target nucleic acid molecule to hybridize to each other and form a double-stranded target-probe complex; (b) nicking the hybridized probe at least once within a predetermined sequence so as to form at least two probe fragments hybridized to the target nucleic acid molecule, resulting in the probe fragments to become single-stranded and allowing the target nucleic acid molecule to become hybridized to another probe; and (c) identifying probe fragments, thereby detecting the target nucleic acid molecule In one embodiment, the invention further provides a method for detecting a target nucleic acid molecule which comprises repeating the above-described steps of (a), (b), and (c). In repeating these steps, the complementary single-stranded nucleic acid probe, which is in an amount greater, i.e., in molar excess, than the target molecule, is allowed to recycle, i.e., hybridize to the target molecule with other nucleic acid probes included in the reaction mixture.

The nucleic acid probe which is useful in the practice of this invention comprises the structure:

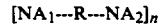

$[NA_1\text{---}R\text{---}NA_2]_n$ wherein $NA_1$ and $NA_2$ are nucleic acid sequences, wherein R is an RNA sequence; and wherein n is an integer from about 1 to about 10.

In one embodiment of this invention, $NA_1$ and $NA_2$, in the nucleic acid probe independently comprise from about 0 to about 20 nucleotides, R comprises from about 1 to about 100 ribonucleotides, or more, and n is an integer from about 1 to about 10.

In another embodiment of this invention, $NA_1$ and $NA_2$ in the nucleic acid probe are DNA sequences. In a further embodiment, $NA_1$ and $NA_2$ in the nucleic acid probe are RNA sequences. In still yet another embodiment, the nucleic acid probe comprises a structure wherein $NA_1$ is either an RNA or DNA sequence, and $NA_2$ is either an RNA or DNA sequence.

In one embodiment, nicking the hybridized probe at predetermined RNA sequences is carried out with a double-stranded ribonuclease. Such ribonucleases nick or excise ribonucleic acid sequences from double-stranded DNA-RNA hybridized strands. An example of a ribonuclease useful in the practice of this invention is RNase H. Other ribonucleases and enzymes may be suitable to nick or excise RNA from RNA-DNA strands, such as Exo III and reverse transcriptase.

The molecules of the present invention may have a detectable marker attached to one or more of the nucleic acid sequences, $NA_1$ or $NA_2$. This marker is contemplated to be any molecule or reagent which is capable of being detected. Examples of such detectable molecules are radioisotopes, radiolabelled molecules, fluorescent molecules, fluorescent antibodies, enzymes, or chemiluminescent catalysts. Another suitable marker is a ligand capable of binding to specific proteins which have been tagged with an enzyme, fluorescent molecule or other detectable molecule. One example of a suitable ligand is biotin, which will bind to avidin or streptavidin.

In one embodiment of this invention, the nucleic acid probe is immobilized on a solid support. In another, the nucleic acid probe is labelled with a detectable marker.

When the nucleic acid sequences, $NA_1$ and $NA_2$ are DNA, the R portion described above may also be properly termed a scissile linkage in language consistent with usage in U.S. Application Ser. No. 805,279, filed Dec. 5, 1985. Such a linkage is capable of being cleaved or disrupted without cleaving or disrupting any nucleic acid sequence of the molecule itself or of the target nucleic acid molecule. As used herein, such a scissile linkage, i.e., R, is any connecting chemical structure which joins two nucleic acid sequences and which is capable of being selectively cleaved without cleavage of the nucleic acid sequences to which it is joined. The scissile linkage may be a single bond or a multiple unit sequence. As used herein, R denotes a ribonucleic acid (RNA) sequence.

In molecules useful as probes in the present invention in which n is greater than one, the unit $NA_1$---R---$NA_2$ repeats. It is contemplated that the unit may be the same within each repeat or it may vary randomly or in a defined pattern. The unit may vary in that $NA_1$ or $NA_2$ or both may vary within each repeat. $NA_1$ or $NA_2$ may vary in that they have different nucleic acid sequences from one repeat unit to the next. This variation may occur randomly such that in every repeat unit, $NA_1$ and $NA_2$, may also vary in that the number of bases of each may vary, either greater or less, from one repeat to the next. This variation may also occur randomly or in a pattern. An example of a random variation where n=3 and both $NA_1$ and $NA_2$ vary is:

$NA_1$---R---$NA_2$---$NA_1'$---R---$NA_2'$---$NA_1''$---R---$NA_2''$

An example of a patterned variation where n=4 and both $NA_1$ and $NA_2$ vary is:
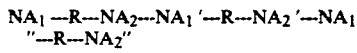
$NA_1$---R---$NA_2$---$NA_1'$---R---$NA_2'$---$NA_1$---R---$NA_2$---$NA_1'$---R---$NA_2'$ In both of the above examples, the solid lines joining each unit are chemical bonds which may be either hydrogen bonds or covalent bonds.

The repeat unit may also vary by variations in the scissile linkage, i.e., R, such that the sequence of ribonucleotides in R, the scissile linkage, will vary. The variation in the sequence of ribonucleotides in R, the scissile linkage, may also be in a random or patterned fashion as discussed above. Also, the repeat units may vary by any combination of the above-mentioned differences in $NA_1$, $NA_2$ or the scissile linkage, i.e., R, and the variations may be random or patterned.

Those skilled in this art will readily appreciate that best results may be achieved with the use of nucleic acid probes whose lengths are relatively short, and therefore, highly specific to the target nucleic acid molecule. By limiting rather than increasing the total number of nucleotides in the complementary nucleic acid probe, high gain-low noise detection of target nucleic acid molecules can be achieved.

Those skilled in this art will readily appreciate that the total length of the nucleic acid probe may vary according to a number of factors including the nature of the target nucleic acid molecule to be detected, the construction of the nucleic acid probe, i.e., whether the probe is a DNA-RNA hybrid or is constructed of RNA sequences alone, and so forth. When the probe is constructed of DNA and RNA sequences, it is important that the R portion or scissile linkage be accessible to nicking or excision in order that a DNA probe fragment remain hybridized to the target nucleic acid molecule. In this regard it is advantageous though not required that the R portion or scissile linkage be located between DNA sequences of from about 8 to about 10 nucleotides in order to allow the probe fragments to become single-stranded in accordance with the method provided by this invention.

When the probe is constructed entirely of RNA sequences, the nicking is facilitated especially when carried out with a double-stranded ribonuclease, such as RNase H or Exo III. Straight RNA probes constructed entirely of RNA sequences are particularly useful because first, they can be more easily produced enzymatically, and second, they have more cleavage sites which are accessible to nicking or cleaving by a nicking agent, such as the aforementioned ribonucleases. Thus, the straight RNA probes do not rely on a scissile linkage as in the DNA-RNA hybrid probes.

The present invention also provides a method for detecting a target deoxyribonucleic acid molecule which comprises: (a) forming a reaction mixture which includes the target deoxyribonucleic acid molecule and a single-stranded nucleic acid probe having a ribonucleotide sequence complementary to the target deoxyribonucleic acid molecule which may be covalently bound at one or both of its termini to one or more deoxyribonucleotides which may or may not be complementary to the target deoxyribonucleic acid molecule under conditions which allow the probe and the target deoxyribonucleic acid molecule to hybridize to each other and form a double-stranded target-probe complex; (b) nicking the hybridized probe at least once within a predetermined sequence so as to form at least two probe fragments hybridized to the target deoxyribonucleic acid molecule, resulting in the probe fragments to become single-stranded and allowing the target nucleic acid molecule to become hybridized to another probe; and (c) identifying probe fragments, thereby detecting the target deoxyribonucleic acid molecule.

In one embodiment, the invention provides a method for detecting a target deoxyribonucleic acid molecule which comprises repeating the above-described steps of (a), (b), and (c).

The single stranded nucleic acid probe useful in method of this invention for detecting a target deoxyribonucleic acid comprises from about 10 to about 2000 ribonucleotides. Those skilled in the art will readily appreciate that the number of ribonucleotides in such a nucleic acid probe may vary widely according to the target deoxyribonucleic acid, the degree of sensitivity required, and so forth. In forming the reaction mixture in step (a) the target deoxyribonucleic acid molecule may have been converted to DNA sequences using methods well-known to those skilled in the art.

In a further embodiment of this invention, nicking the hybridized probe in step (b) is carried out with a double-stranded ribonuclease. In still yet a further embodiment such a ribonucleases may be RNase H. There are other enzymes having RNase H-like activity, such as Exo III and reverse transcriptase and so forth. These enzymes and others may be suitable, with or without modification to the methods described herein.

In forming the reaction mixture in step (a) above, the target nucleic acid molecule and an amount of a complementary single-stranded nucleic acid probe which is greater, i.e., in molar excess, than the target molecule, are mixed together under hybridizing conditions which allow the probe and the target to hybridize to each other and form a double-stranded target-probe complex.

Nicking the hybridized probe in step (b) above can be carried out enzymatically, for example, by contacting the hybridized probe with an agent capable of nicking, i.e., excising out, predetermined sequences in the hybridized probe. Such predetermined sequences in the practice of this invention include the scissile linkages, i.e., R, or RNA sequences.

Typically the target nucleic acid molecule and the labelled complementary single-stranded nucleic acid probe, which is in excess to the target molecule, are combined in a reaction mixture with an appropriate buffer. The reaction mixture so formed is incubated at a temperature, of from about 30° to about 45° C., optimally at about 37° C. for from about 5 to about 30 minutes, up to about 60 minutes or how ever long a period of time is required to effect annealing.

The reaction mixture which includes the hybridized target and probe is next combined with a nicking agent also at a temperature of from about 30° to 45° C., optimally at about 37° C. for an additional amount of time. The additional amount of time may vary from about 5 to about 60 minutes although 30 minutes is sufficient in most cases. The cycling reaction which involves repeating the steps of hybridizing, nicking and causing single-stranded probe fragments to form takes place in a short period of time, e.g., on the order of milliseconds.

By nicking the hybridized double-stranded target-probe complex at least once within a predetermined sequence, e.g., in R or the scissile linkage, so as to form at least two probe fragments hybridized to the target nucleic acid molecule, the remaining hybridized probe fragments will become single-stranded as the result of the change in size of the hybridized probe sequences in the target-probe complex. For example, a 20 mer (monomer) double-stranded DNA sequence will remain annealed or hybridized at 37° C. After nicking, assuming that an intervening 4-ribonucleotide (RNA) base sequence between two 8-deoxyribonucleotide (DNA) base sequences is excised by a ribonuclease, e.g., RNase H or Exo III, the remaining two 8-mer hybridized probe fragments will melt or fall off the target-probe complex. These single-stranded probe fragments may then be identified using well-known methods, thereby detecting the target nucleic acid molecule.

A=T and G=C base-pairs exhibit $T_m$s of approximately 2°/base-pair and 4°/base pair, for short olgomers respectively. On the average, assuming equal ratios of A-T and G-C base pairs in a hybridized target-probe complex, each paired nucleotide exhibits a melting point temperature of approximately 3°/base-pair.

Identifying the probe fragments and thereby detecting the target nucleic acid molecule in step (c) may be performed using a number of methods. The method of identification and detection in step (c) will depend on the type of labelling or detectable marker which has been placed on the nucleic acid probe or which is generated in step (b) above. For example, detection of the target nucleic acid molecule may be performed by coupling to a fluorescent label or by ATP generation. Where, for example, a probe is constructed entirely of ribonucleic acid (RNA) sequences, the probe fragments which result from the nicking step (b) may range from mononucleotides to short olignucleotides. Such fragments will possess unique 5' phosphate groups which may be advantageously used in their detection. Among such fragments are 5' adenosine monophosphate (5'-AMP) which may be fed into an enzymatic ATP generating system and subsequently linked to a luciferin-luciferase photometric read out system. As an alternative method of detection, the generated probe fragments may be detected directly using, for example, high performance liquid chromatography (HPLC).

Those skilled in the art will further appreciate that the methods of the present invention may be employed to obtain a high gain-low noise amplification system for detecting target nucleic acid molecules. The single-stranded nucleic acid probe, whether constructed of deoxyribonucleic acid (DNA) and ribonucleic acid (RNA) sequences, or ribonucleic acid (RNA) sequences alone, is completely stable to the action of certain double-stranded ribonucleases, e.g., RNase H. When such a probe is hybridized to a target nucleic acid molecule, the RNA link, which may or may not be a scissile linkage, becomes susceptible to digestion by the ribonuclease, e.g., RNAse H.

Taking as an example for illustrative purposes only, a probe of an overall length of 20 nucleotides of which the first eight and last eight nucleotides are deoxyribonucleotides and the intervening four nucleotides are ribonucleotides, the amplifying aspect of the methods of this invention may be explained. A 20 mer, (monomer) probe will form stable hybrids with a complementary target whereas an 8 mer (monomer) probe or probe fragment is easily melted off, i.e., becomes unhybridized, under the same conditions. Consequently, the 20 mer probe after hybridization to the target nucleic acid molecule, becomes cleavable and is cleaved by the ribonuclease, e.g., RNase H, resulting in pieces which readily melt off under the identical conditions of the primary hybridization in which the single-stranded nucleic acid probe became hybridized to the target molecule to form the double-stranded target-probe complex.

If hybridization is carried out with a customary excess of probe and in the presence of a suitable ribonuclease, e.g., RNase H, the system described above will cycle (see FIG. 1) and generate cleaved probe fragments, which may be detected using a number of well-known methods, e.g., chemiluminescence, radio-isotopes. The primary amplifier, i.e., the probe, is nucleic acid specific and will operate under constant conditions. High gain-first stage detection of $10^{-20}$ moles of target with a radio-isotope label may be obtained.

In a situation where a straight RNA probe made entirely of ribonucleic acid sequences has been constructed, the resulting products after RNase H cycling will rnage from mononucleosides upwards to oligonucleotides depending on the size of the original probe. Each product, however, will have a 3'-OH terminus. These termini can be tailed with a suitable polymerase such as polynucleotide phosphorylase orpoly A polymerase.

A useful adjunct to this approach is to have a biotin on the 5' terminus of the probe and a chain terminating nucleotide on the 3' terminus e.g., dideoxy. If the probe was designed so as to have a "U" at the 5' terminus and a "U" at the 3' terminus but with no other "U"s contained within the central region and if this probe was made by the action of T7 RNA polymerase on a suitable termplate, the following situation would hold:

```
                                            No ACG
Probe transcript  5' U(N N N N N N N N)ₓU 3'
3' T7 Polymerase    A(N N N N N N N N)ₓA 5'
  Binding Site                          ↑
                                 Restriction Site
                                 For Run Off
                                 Transcription
                                 (optional)
```

If the nucleoside triphosphate precursors for the T7 transcript (probe) polymerization are in the ratio of 100 ATP
100 CTP
100 GTP
100 Dideoxy UTP
1 Biotinylated UTP then virtually every probe transcript will begin with biotinylated U and end with dideoxy U. Polymerization will fail if a dideoxy U is selected for the first base. Thus a start with biotinylated UTP is mandatory. Because, with excess template, almost all the biotinylated U will be used for starting and because the dideoxy U is 100 times in excess over the biotinylated U, the 3' U will almost always be a dideoxy U. Hence, detection goals may be obtained via an enzymatic synthesis. The resulting probe cannot be tailed unless cut by RNase H because of the 3' dideoxy U and the biotin can be used to separate the probe, which is now tailed with a fluorescent base or other detectable moiety, from non-biotinylated reactants.

When the nucleic acid probe is constructed entirely of RNA sequences complementary to the target molecule and, therefore, not dependent on the scissile link, various modifications in the probe may be made which are fully contemplated by the invention described herein.

For example, a ribonucleic acid probe, i.e., constructed entirely of RNA sequences, may be synthesized and its 3' hydroxyl end optionally blocked. Blocking may be effected by enzymatically producing a "tail" to the ribonucleic acid probe by attachment to a ligand, such as biotin, periodate oxidized ribonucleoside or an affinity tail, e.g., poly A (polymerase A) tailing. The "tail" to the probe may be used for affinity isolation and for signal generation. The 5' end of the RNA probe may likewise be optionally modified. For example, the 5' end may be extended with non-homologous RNA/DNA sequences which, in turn, may be attached to a ligand, as described above, e.g., biotin, periodate oxidized ribonucleoside or an affinity tail. In this particular embodiment, the 5' end could instead be linked to a signal generator such as a fluorescent base. This arrangment is shown below:

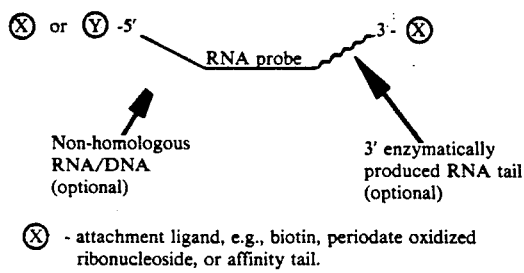

Ⓧ - attachment ligand, e.g., biotin, periodate oxidized ribonucleoside, or affinity tail.

Ⓨ - signal generator such as a fluorescent base

The nonhomologous 5' tail in such an arrangment allows the ribonuclease, e.g., RNase H, to nick, i.e., excise or chew up, the homologous region of the RNA probe which has paired with the target. Thus the 5' tail arrangement leaves a fragment available for polynucleoside phosphate (PNP) or polymerase A (poly A) tailing. Such a tail may be used as an affinity tail to pull the signal out of solution or as a further fragment to enhance detection. This arrangement is depicted below:

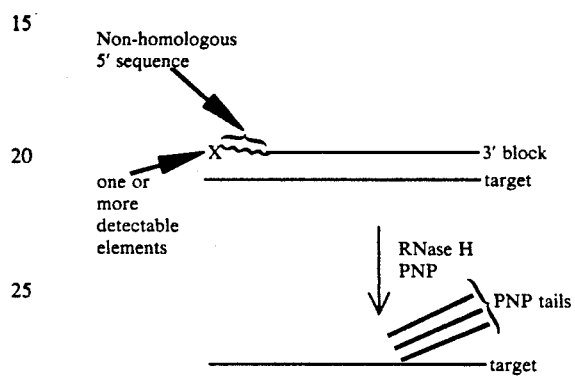

In another feature of this invention, the cycling nucleic acid probe may be used in immunoassays to detect antibodies or atigens. In this situation, a nucleic acid sequence, which could be a homopolymer, may be attached to either an antibody or antigen in competing or non-competing immunoassays:

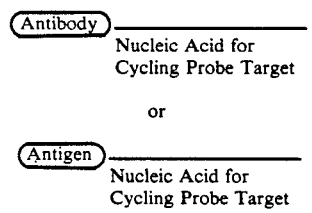

An example of a competing immunoassay is the enzyme linked immunoassay (ELISA).

This invention is illustrated in the examples which follow. These examples are set forth to aid in the understanding of the invention but are not intended to, and should not be construed to, limit in any way the invention as set forth in the claims which follow thereafter.

EXAMPLE 1

CONSTRUCTION OF SCISSILE LINK PROBES

Probe molecules useful in the detection methods of this invention have been constructed on a solid support medium (either silica gel or controlled pore glass) using either a hydrolysable linkage or a permanent (non-hydrolysable) linkage. Published chemical methods were used for this synthesis. (Alvarado-Urbina, G., G. M. Sathe, W. C. Liu, M. F. Gillan, P. D. Duck, R. Bender, and K. K. Ogilvie (1981), Automated Synthesis of Gene Fragments, Science 214: 270-274; Roberts, D. M., R. Crea, M. Malecha, G. Alvarado-Urbina, R. H. Chiarello, and D. M. Watterson (1985), Chemical Synthesis and Expression of a Calmodulin gene designed for a Site-Specific Mutagenesis, Biochemistry, in press;

Van Boom, J. H., and C. T. Wreesman (1984), Chemical Synthesis of Small Oligoribonucleotides in Solution, In Oligonucleotide Synthesis—A Practical Approach, pp. 153-183, Ed. M. J. Gait, IRL Press). Standard protected deoxynucleoside monomers were obtained from commercial sources whereas protected deoxyuridine and the ribonucleoside whereas protected deoxyuridine and the ribonucleoside monomers were prepared using published procedures. (Ti, G. S., B. L. Gaffney, and R. A. Jones (1982), Transient Protection: Efficient One Flask Synthesis of Protected Nucleosides, J. AM. Chem. Soc. 104: 1316). Synthesis was performed with a BIOLOGICALS automated synthesizer using a cycle time of 10 minutes for each DNA condensation and 12 minutes for each RNA condensation.

The following probe constructions were used in various test systems.

Scissile Link Probes

P. L. = Permanent Linkage to Solid Support
H. L. = Hydrolysable Linkage to Solid Support 1. MRC046:
   5'd(TTTTTTTTTT)r(UUUUU-U)d(TTTTTTTTTT)3'- P.L.
2. MRC059:
   5'd(TTTTTTTTTT)r(UUU-U)d(TTTTTTTTTTTT)3'- H.L.
3. MRC060:
   5'd(TTTTTTTTTTTT)R(UUU-U)D(TTTTTTTTT)3'- H.L.
4. MRC064:
   5'd(TTTTTTTTTTTT)d(UUUUUUU-U)d(TTTTTTTTT)3'- H.L.
5. MRC068:
   5'd(TTTTTTTTTTTTTT)d(UUUUUUU-U)d(TTTTTTTTT)3'- H.L.
6. MRC069:
   5'd(GGGTAACGCCAG)r(GGUUUU)d(CCAGTCAC)3'- H.L.
7. MRC070:
   5'd(GGGTAACGCCAG)r(GGUUUU)d(CCAGTCAC)3'- P.L.
8. MRC071:
   5'd(TTTTTTTTTTTTTTTT)r(U-U)d(TTTTTTTTTT)3'- H.L.

Probe molecules 1-3 and 5-8 were shown to be cleavable at the ribonucleotides by a number of RNases including pancreatic RNase as well as by basic conditions (e.g., 0.5M NaOH). Most general methods for cleavage by RNases and other routine procedures can be found in Maniatis et al. (Maniatis, T., E. F. Fritsch, and J. Sambrook, (1982), Molecular Cloning, A Laboratory Manual, Cold Spring Harbor Laboratory).

EXAMPLE 2

The following probe constructions* were used in accordance with the methods provided by this invention:

*Upper case letters are DNA. Lower case letters are RNA. Some of the above sequences were M-13 phage complements but all had synthetic DNA target complements constructed for them.

261 (9) 5' C C A G G G T T u u c c c A G T C A C G 3'

268 (10) 5' A C G C C A G G G T T T T C C c a g T C A C G A C 3'

271 (11) 5' C A G G G T T u g a u c a G T C A C G A C 3'

276 (12) 5' T A C A A A C A c c c c C A A T A T T G 3'

284 (13) 5' T A G A C T T T g c a a C T C T T G G T 3'

286 (14) 5' a c a a a c a c c c c c a a u a u u 3'

287 (15) 5' C C A G G g g u T T T C c c a G T C A 3'

293 (16) Biotin ~ 5' C C A G G G T T u u c c C A G T C A C G 3'

296 (17) 5' T T T T T T T g g g g T T T T T T T 3'

300 (18) 5' T T T T T T T c c c c T T T T T T T 3'

308 (19) 5' T A G C T T a a u a a T T C G A T 3'

311 (20) 5' C A G T G C a a c a a A G T G C G

313 (21) 5' G A C T G C a c a c a A G T G C A

316 (22) 5' G T T T A A A g u c u g C C C A A G A 3'

Kination and Cycling and RNase H

2 μg of the electropurified probes (9-22) were placed in a mixture containing the following:

| | |
|---|---|
| 2 μg probe | 2 μl |
| 4 μM ATP | 4 μl |
| 10X KB (Kinase buffer) | 5 μl |
| dH$_2$O | 32 μl |
| P$^{32}$ ATP | 2 μl = 20 uCi |
| Polynucleotide Kinase | 5 μl = 5 units |

The mixture was incubated at 37° C. for 40 minutes and then heat inactivated. The mixture was then passed through a Sephadex G-50 column using deionized water as an eluent. (Use Sanco transfer pipettes 15 mm × 7.5 mm as disposable columns. Plug with siliconized glass wool and pack with G-50 up to 12 mm.)

500 μl fractions were collected into 1.5 ml Eppendorf tubes and the first peak was selected (usually tubes 3-5). The selected fractions were dried in a speed vac concentrator. The tubes were pooled together to give a final concentration of 0.1 μg/μl in sterile water.

Dilution for Cycling Reaction

Target: 2 μg are diluted in 20 μl to give a concentration of 0.1 μg/μl. This initial concentration is serially diluted 1:10 (10 μl in 90 μl distilled water) to the desired concentrations. For the cycling reaction, 10 μl (100 ng) were used for each reaction.

Labelled Probe: 2μ are diluted in 20 μl (0.1 μg/μl). This initial concentration is diluted 1:10 (10 μl in 90 μl distilled water) to 0.01 μg/μl. 10 μl (100 ng) were used for each reaction.

Cycling Reaction

For the cycling reaction, each of the probes(9-22) were separately placed in the following reaction mixture:

10 μl (100 ng) of probe in distilled water(sterile)
3 μl 10X RNAse H buffer
7 μl distilled water
10 μl target DNA (1 μg to 0.01 fg)

The 30 μl reaction mixture was incubated at 65° C. for 10 minutes and at 37° C. for 30 minutes. From each 30 μl reaction mixture, the following were taken:

C1 (RNAse H) control—5 μl = 16.7 ng probe

C2 (30 min. time) control—5 μl=16.7 ng probe
To the remaining 20 μl of reaction mixture, the following were added with Control C1 above:
1 μl RNase H at 0 minutes time
1 μl RNase H at 10 minutes time
1 μl RNase H at 20 minutes time.
The reaction mixture was incubated for 30 minutes. Each reaction was loaded with the same amount of probe as the control plus an equal amount of formamide dye on a 0.8 mm 20% acrylamide/7M urea gel at 800 volts with a heating plate.

What is claimed is:

1. A method for detecting a single-stranded target nucleic acid which comprises:
   (a) obtaining the single-stranded target nucleic acid;
   (b) forming a reaction mixture which includes the target nucleic acid and a complementary single-stranded nucleic acid probe under conditions which allow the target nucleic acid and the probe to hybridize to each other and form a double-stranded, target-probe complex, the probe being present in molar excess relative to the target and having the structure $[NA_1 - R - NA_2]_n$ wherein $NA_1$ and $NA_2$ are DNA sequences, wherein R is a scissile nucleic acid linkage, and wherein n is an integer from 1 to 10;
   (c) treating the double-stranded, target-probe complex from step (b) so as to cleave the probe within a predetermined sequence of the scissile nucleic acid linkage and thereby form at least one intact DNA-containing oligonucleotide fragment from the probe, such fragment being, or being treated so as to be, no longer capable of remaining hybridized to the target nucleic acid;
   (d) repeating steps (b) and (c); and
   (e) detecting the intact DNA-containing fragments so formed and thereby detecting the single-stranded target nucleic acid.

2. A method of claim 1, wherein the oligonucleotide fragment in step (c) is labelled with a detectable marker and labelled fragments are detected in step (e).

3. A method of claim 1, wherein the oligonucleotide fragment in step (c) is unlabelled, but capable of being labelled with a detectable marker, the fragment is so labelled prior to step (d) or (e), and labelled fragments are detected in step (e).

4. A method of claim 1, wherein the scissile nucleic acid linkage is an RNA sequence.

5. A method of claim 1, wherein $NA_1$ and $NA_2$ independently comprise from 0 to about 20 deoxyribonucleotides and R comprises for 1 to about 100 ribonucleotides.

6. A method of claim 1, wherein n is an integer from 2 to 10 and wherein at least one of $NA_1$ or $NA_2$ varies within the probe.

7. A method of claim 1, wherein n is 1.

8. A method of claim 1, wherein the treating in step (c) comprises contacting the double-stranded target-probe complex with a double-strand-specific ribonuclease.

9. A method of claim 8, wherein the ribonuclease is RNase H.

10. A method of claim 8, wherein the ribonuclease is Exo III.

11. A method of claim 1, wherein the probe is immobilized on a solid support.

12. A method of claim 3, wherein the unlabelled fragment has a 3'-hydroxyl group and wherein the labelling of the fragment comprises RNA tailing from the 3'-hydroxyl group.

* * * * *